United States Patent

Small et al.

Patent Number: 6,061,582
Date of Patent: *May 9, 2000

[54] METHOD AND APPARATUS FOR NON-INVASIVE DETERMINATION OF PHYSIOLOGICAL CHEMICALS, PARTICULARLY GLUCOSE

[75] Inventors: Gary W. Small, The Plains, Ohio; Mark Arnold, Iowa City, Iowa

[73] Assignees: University of Iowa Research Foundation, Iowa City, Iowa; Ohio University, Athens, Ohio

[ * ] Notice: This patent is subject to a terminal disclaimer.

[21] Appl. No.: 08/860,850

[22] PCT Filed: Feb. 7, 1995

[86] PCT No.: PCT/US95/01556

§ 371 Date: Jun. 11, 1997

§ 102(e) Date: Jun. 11, 1997

[87] PCT Pub. No.: WO95/22046

PCT Pub. Date: Aug. 17, 1995

Related U.S. Application Data

[63] Continuation-in-part of application No. 08/195,709, Feb. 14, 1994, Pat. No. 5,459,317.

[51] Int. Cl.[7] .................................................. A61B 5/00
[52] U.S. Cl. ................................ 600/316; 600/322
[58] Field of Search ............................ 600/310, 314–316, 600/322, 323, 326–328, 339, 341, 473, 476, 478; 356/39–41

[56] References Cited

U.S. PATENT DOCUMENTS 5,372,135 12/1994 Mendelson et al. .................... 600/322
5,459,317 10/1995 Small et al. ......................... 250/341.1

OTHER PUBLICATIONS

Arnold et al., "Determination of Physiological Levels of Glucose in an Aqueous Matrix with Digitally Filtered Fourier Transformed Near–Infrared Spectra," Analyticl Chemistry 62, 1457–1464, 1990.

Small et al., "Design of Optimized Finite Impulse Response Digital Filters for Use with Passive Fourier Transform Infrared Interferograms", Analytical Chemistry 62, 1768–1777, 1990.

*Primary Examiner*—Linda C. M. Dvorak
*Assistant Examiner*—Bryan K. Yarnell
*Attorney, Agent, or Firm*—Oppedahl & Larson, LLP

[57] ABSTRACT

Non-invasive measurements of physiological chemicals such as glucose in a test subject are made using infrared radiation and a signal processing system. The level of a selected physiological chemical in the test subject is determined in a non-invasive and quantitative manner by a method comprising the steps of: (a) irradiating a portion of the test subject with near infrared radiation; (b) collecting data concerning the irradiated light on the test subject; (c) digitally filtering the collected data to isolate a portion of the data indicative of the physiological chemical; and (d) determining the amount of physiolgocial chemical in the test subject by applying a defined mathematical model to the digitally filtered data. The collected data is in the form of either an absorbance spectrum or an interferogram.

16 Claims, 10 Drawing Sheets

METHOD AND APPARATUS FOR NON-INVASIVE DETERMINATION OF PHYSIOLOGICAL CHEMICALS, PARTICULARLY GLUCOSE

RELATED APPLICATION

This application is a continuation-in-part of application Ser. No. 08/195,709 filed Feb. 14, 1994, now U.S. Pat. No. 5,459,317, and a 371 of PCT/US95/01556, filed Feb. 7, 1995 published Aug. 17, 1995.

The invention described in this application has been developed in part with funds received from the US National Institutes of Health under grant number DK 45126. The United States Government may have certain rights under this invention.

BACKGROUND OF THE INVENTION

This application relates to a method and apparatus for the non-invasive, quantitative measurement of physiological chemicals, particularly glucose, in a patient.

Determination of blood glucose is a routine procedure performed several times a day by many diabetics. In general, this procedure involves the taking of a small blood sample and evaluating the level of glucose in the sample. Common instruments used for this purpose use the enzyme glucose oxidase to convert glucose and oxygen to gluconic acid and hydrogen peroxide, and then measure the level of peroxide by either spectroscopic or electrochemical means.

While these daily measurements provide the diabetic patient with the ability to self-monitor and thus better control blood glucose levels, they are not without drawbacks. In particular, the taking of blood samples several times a day can be painful and exposes the patient to a risk of infection. Moreover, using this existing technology it is impossible to obtain a continuous blood glucose measurement. Thus, during the night, a patient must either be awakened periodically for testing or run the risk that glucose levels will drop to dangerous levels as they sleep.

In view of the foregoing, there exists a real need for a non-invasive method of measuring blood glucose in a patient. It has been suggested that this could be accomplished using near-infrared (NIR) radiation. Thus, U.S. Pat. No. 5,086,229 of Rosenthal, which is incorporated herein by reference, describes a system using a plurality of infrared light emitting diodes and a detector to measure blood glucose. The infrared measurement of glucose in the body is immensely complicated, however, because of the substantial absorbances of fats and proteins in the near-infrared. Thus, while the Rosenthal patent presents an interesting theory, there is no published documentation that demonstrates the ability of the Rosenthal system to measure glucose noninvasively. Furthermore, the wavelengths used in the Rosenthal system have never been shown to possess useful glucose information.

It is an object of the present invention to provide a practically useful non-invasive near-infrared detector for blood glucose and other physiological chemicals that is adaptable for continuous use.

It is a further object of the present invention to provide a method for the non-invasive quantitative measurement of physiological chemicals and particularly glucose in a patient that can be used either continuously or intermittently.

It is still a further object of the invention to provide an apparatus for continuous or intermittent non-invasive monitoring of blood glucose and other physiological chemicals in a patient.

SUMMARY OF THE INVENTION

In accordance with the invention, non-invasive measurements of physiological chemicals such as glucose are made using infrared radiation and a signal processing system that permits the construction of a device suited for home use. Thus, the level of a selected physiological chemical in a test subject is determined in a non-invasive and quantitative manner by a method comprising the steps of:

(a) irradiating a portion of the test subject with near-infrared radiation such that the radiation is transmitted through or reflected from the test subject;

(b) collecting data concerning the transmitted or reflected infrared radiation using a detector;

(c) digitally filtering the collected data to isolate a portion of the data indicative of the physiological chemical; and (d) determining the amount of physiological chemical in the test subject by applying a defined mathematical model to the digitally filtered data. The data collected may be in the form of an absorbance spectrum, i.e., a representation of the variation in absorbance as a function of wavelength; or in the form of an interferogram, i.e., a representation of infrared light intensity as a function of the retardation of the moving mirror in the interferometer, and thus of time.

In a further aspect of the invention, there is provided a device for measurement of a chemical in a sample comprising:

(a) means for collecting data concerning near-infrared radiation transmitted through or reflected from the sample;

(b) means for digitally filtering the collected data to isolate a portion of data indicative of the chemical;

(c) means for applying a defined mathematical model to the digitally filtered data, whereby the amount of chemical in the test subject is determined; and (d) means for reporting the amount of chemical in the sample. This device can be incorporated into a complete apparatus for the non-invasive measurement of blood glucose. Such an apparatus would also include a source of infrared radiation and a mechanism for directing the infrared radiation from the source to the test subject and from the test subject to the means for collecting the spectrum.

DETAILED DESCRIPTION OF THE INVENTION

Figure 1:
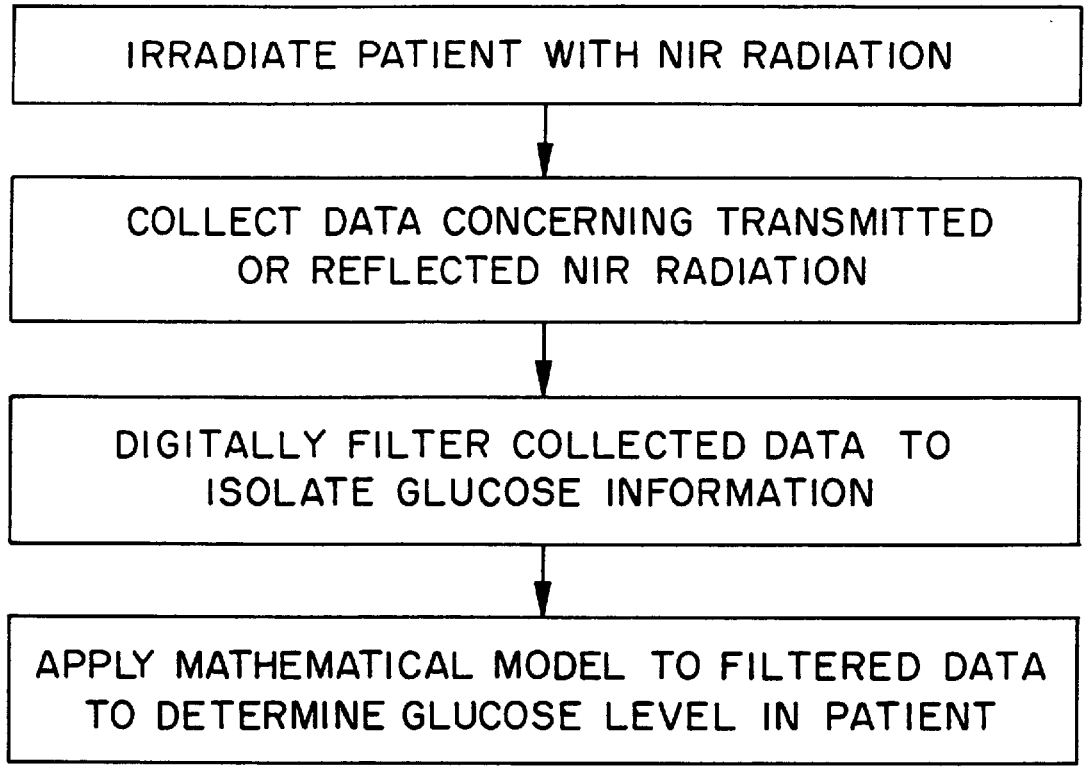
FIG. 1 is a flow chart depicting the method of the invention.

FIG. 1 is a flow chart depicting the method of the invention, as applied to the non-invasive determination of blood glucose in a human patient. As shown, the first step of the method is the irradiation of the test subject, in this case the patient, with near-infrared radiation.

Suitable NIR radiation for use in the present invention coincides with the absorbance bands of glucose or other physiological chemical being measured. For glucose, these bands are located in the regions of 5000–4000 $cm^{-1}$ and 6500–5800 $cm^{-1}$. The intensity of the light at the selected wavelength should be on the order of 700 lux or greater. Such radiation can be produced by a 300 W tungsten-halogen lamp.

Since the spectrum obtained and used in the method of the present invention may be either a transmittance spectrum or a reflectance spectrum, considerable latitude is available in the manner and location in which the NIR radiation impinges on the test subject. For example, if transmitted NIR radiation is being measured, the NIR radiation should impinge on a relatively thin, fleshy area of the patient such as the fleshy webs between the fingers or toes or the ear lobe. If reflectance spectra are to be used, the sampling site should be characterized by high blood flow close to the surface, such as the ventral surface of the wrist.

The source of NIR radiation used in the present invention may be such that it is disposed directly against the surface of the test subject. For example, a small halogen lamp could be used. Alternatively, the source may be physically remote from the test subject. In the latter case, it is advantageous, although not necessary, to guide the NIR radiation to the desired irradiation site on the surface of the test subject, for example by means of optical fibers.

In the second step of the method, the data concerning the transmitted or reflected NIR radiation is collected using a detector. The specific nature of the detector is not critical, provided it is capable of detecting the pertinent wavelengths of light and responding rapidly enough to be compatible with the other components of the device. An example of a suitable detector for collection of an absorbance spectrum is a combination of a dispersive element, e.g., a grating or prism, and an optical multi-channel analyzer sensitive to NIR radiation. In the case where the data is to be collected as a single beam spectrum, an absorbance spectrum or an interferogram, a suitable detector is a combination of a NIR interferometers and a photon counting detector such as a solid state indium antimonide detector.

The positioning of the detector relative to the test subject will depend both on the nature and size of the detector and the environment in which the measurement is being taken. For most purposes, it will be desirable to have the detector physically separated from the test subject, both because of detector size and to maximize detector performance by providing the detector with a stable environment. It will therefore generally be advantageous to guide the transmitted or reflected NIR radiation to the detector, for example using optical fibers.

Depending on the instrumentation selected, the data concerning the transmitted or reflected radiation is collected as either an absorbance spectrum or an interferogram. In either case, the next step as shown in FIG. 1 is to digitally filter the data to isolate the portion of the data which is indicative of the chemical of interest. The specific manner in which this step is performed depends on the form of the collected data.

Digital Filtering of an Absorbance Spectrum

Figure 2:
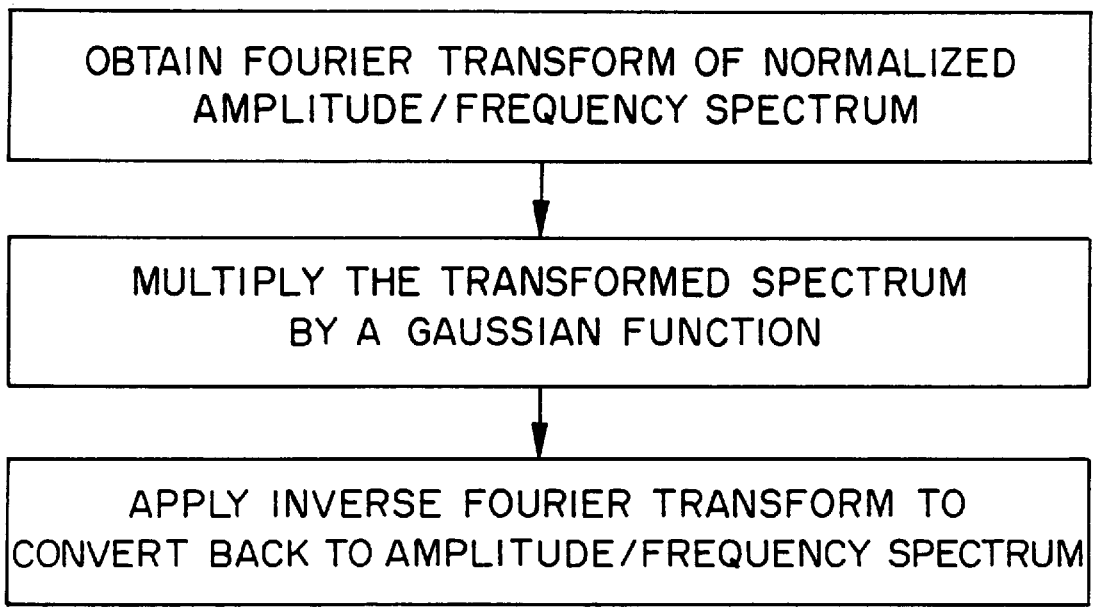
FIG. 2 is a flow chart depicting a process for digitally filtering an absorbance spectrum.

When the data collected is in the form of an absorbance spectrum, the process for filtering the data is shown in FIG. 2. As shown, the absorbance spectrum, or a portion thereof containing information about the chemical being tested for, is transformed using a Fourier transform into a Fourier domain spectrum The transformed spectrum is then filtered by multiplying it by a Gaussian function that weights spectral information associated with the chemical being analyzed. In the case of glucose, a suitable Gaussian function is defined by a mean position of 0.037 f (digital frequency units) and a standard deviation width of 0.011 f. This function emphasizes a glucose-associated absorbance band appearing in the spectral region between 6500 and 5800 $cm^{-1}$. Other peaks, and other Gaussian functions for the same peak may also be employed. For example, the glucose-associated absorbance band at 4400 $cm^{-1}$ can be emphasized. For physiological chemicals other than glucose, appropriate Gaussian functions may be identified. For absorbance spectra processing, the proper Gaussian function can be obtained by analyzing the shapes of the absorbance bands for the compound of interest. After multiplication of the spectrum with the Gaussian function, the resulting filtered spectrum is converted back to an absorbance spectrum using an inverse Fourier transform.

While the use of a Fourier filtering process such as that described above is a preferred method of performing the method of the invention, other digital filtering methods may also be used. Such methods include finite impulse response and infinite impulse response digital filters.

Digital Filtering of a Single Beam Spectrum or an Interferogram

An important aspect of non-invasive measurement of glucose and other physiological chemicals using interferograms is the ability to analyze this data in the absence of a contemporaneously collected background or reference spectra. This is the case because no convenient method exists to collect a background spectrum such as the spectrum of a particular human subject without glucose.

When the data concerning the transmitted or reflected infrared radiation is collected in the form of an interferogram, it may be processed in either of two general ways. First, the interferogram may be converted to a conventional single beam spectrum using a Fourier transform and then filtered by multiplication with an appropriate Gaussian function. For example, in the case of a noninvasive determination of glucose, a Gaussian function having half-power points of 4445.4 and 4354.6 cm$^{-1}$ can be used to emphasize the glucose absorbance band at 4400 cm$^{-1}$. This corresponds to a Gaussian function having a mean position of 0.139 f and a standard deviation of 0.00122 f. Other Gaussian functions for digital filtering to obtain information from other glucose absorbances or for absorption bands associated with other chemicals of interest can be obtained by matching functions to the width and location of the absorption bands.

This filtering differs from the process described above, in that ratioing to eliminate the background signal is not performed. Because of this, after multiplication of the transformed spectrum, the resulting filtered spectrum can be subjected to an inverse Fourier transformation to yield a filtered interferogram. Such an interferogram is much simpler in appearance than the original interferogram, because much of the noise and absorbances not associated with the chemical of interest have been removed. Further, there is a clear correlation between the magnitude of the interferogram signal and the amount of the chemical being measured in the test subject.

The magnitude of the interferogram peaks is advantageously measured by the simple procedure of integrating the interferogram to determine the total power of the signal. This yields a single value related to the glucose concentration. Alternatively, the individual points in the filtered interferogram could be submitted to a multivariate calibration method such as a partial least squares regression. This would yield a multivariate model relating the individual interferogram point intensities to glucose concentration.

Alternatively to transforming the interferogram into a single beam spectrum, the interferogram itself may be subjected to a digital filtering process, and the magnitude of the filtered interferogram peaks analyzed using a predefined mathematical model. We have defined a model which predicts an approximately linear relationship between analyte concentration and filtered interferogram intensity as given by the formula $$C \sim NP$$

where C is the concentration, P is the magnitude of the filtered segment, and N is a sensitivity term defined as $$N = \frac{1}{\sqrt{\sum_{k=n_1}^{n_2} Z[k]^2}}$$

where Z[k] is an interferogram domain function. The approximate linear relationship between the analyte concentration and magnitude of the filtered interferogram segment is based on the assumption that a MacLaurin series approximation used in the derivation of the relationship is valid. This approximation only holds for small absorbance values. For example, Sparks et al., *Anal. Chem.* 54: 1922–1926 (1982) have estimated that this approximation has less than 5% error if the absorbance value is less than 0.12. For glucose analysis using the present invention, peak absorbance of the glucose band is on the order of $10^{-4}$ or less. Thus, the use of this approximation appears valid.

The approximate linear relationship also depends on the value of N being substantially constant across the calibration samples. This requires that the sample pathlength, molar absorptivity and the intensity of the filtered reference spectrum be constant with respect to concentration.

Variation in sample pathlength is not a problem in laboratory measurements due to the use of a fixed pathlength sample cell. It could present more of a problem in actual noninvasive tests performed on body tissue. Moreover, since the entire spectral band is isolated by the bandpass filter rather than a single wavenumber, some change in molar absorptivity might be expected across the concentration range. These two factors could lead to limitations on the dynamic range over which the linear relationship would hold, potentially making several calibration factors necessary. They should not, however, prevent the use of the linear approximation for making noninvasive glucose determinations.

The assumption of constant intensity of the filtered reference spectrum is problematical, as some variation in infrared intensity is common in a Fourier transform infrared experiment due to changes over time in instrumental characteristics such as interferometer alignment and detector temperature. These factors can be overcome through the use of a normalization step.

Finally, the linear relationship set forth above assumes that only a single analyte band has been isolated by the bandpass filter. If other analyte bands or bands from other constituents in the sample matrix fall within the filter bandpass, their interferogram signatures will add to the signature of the targeted analyte band. The filtered interferogram will then possess a more complex structure and the simple univariate linear relationship will not apply. The selection of an appropriate bandpass filter is therefore quite important to the success of the direct measurement of interferogram intensity as a method for noninvasive determination of physiological chemicals. If suitable filters cannot be identified for a given analyte and sample matrix, however, a multivariate analysis procedure can be used on place of the linear approximation as discussed in Examples 4 and 5 herein.

Application of digital filtering directly to the interferogram depends on the fact that each wavelength of light is represented in the interferogram by a modulated sine wave whose frequency (in hertz) depends on the wavelength of the light and the interferometer mirror velocity in accordance with the equation $$\frac{frequency}{of\,signal} = 2 \times \frac{wavenumber}{of\,radiation} \times \frac{mirror}{velocity}$$

where the wavenumber has units of cm$^{-1}$, the mirror velocity is expressed in units of cm/sec. By selecting an electronic filter that selects out only the portion of the interferogram having the frequency defined by this equation for the selected absorbance of the chemical being measured, a simplified interferogram is obtained.

The construction of electronic filters to select for specified wavelengths is commonplace in the electronic arts. Briefly, the filter would be implemented as a digital filter. The software controlling the device would implement the filter as part of the data processing. The digital filter used implements an approximation of the convolution sum $$y[n] = \sum_{k=-\infty}^{\infty} x[k]h[n-k]$$

where y[n] is the filtered interferogram at point n, x[k] is the original unfiltered interferogram at point k, and h[n-k] are points on the impulse response of the digital filter, i.e., the interferogram-domain representation of the frequency response filter.

While the digital filtering procedure for interferograms has been described above in terms of a Fourier filtering process, other digital filtering methods may also be used. In particular, methods such as finite impulse response and infinite impulse response filters can be used. These filter design methods approximate the infinite summation in the convolution sum above. These methods offer the advantage of reducing the size of the interferogram required, which can lower the performance requirements of the interferometer.

While the method of the invention can be practiced on complete interferograms, it has been found that short segments of an interferogram can be used as well. This has great significance to the application of this technology in relatively rigorous environments, because it facilitates the construction of a smaller interferometer with less stringent mechanical tolerances.

Figure 3:
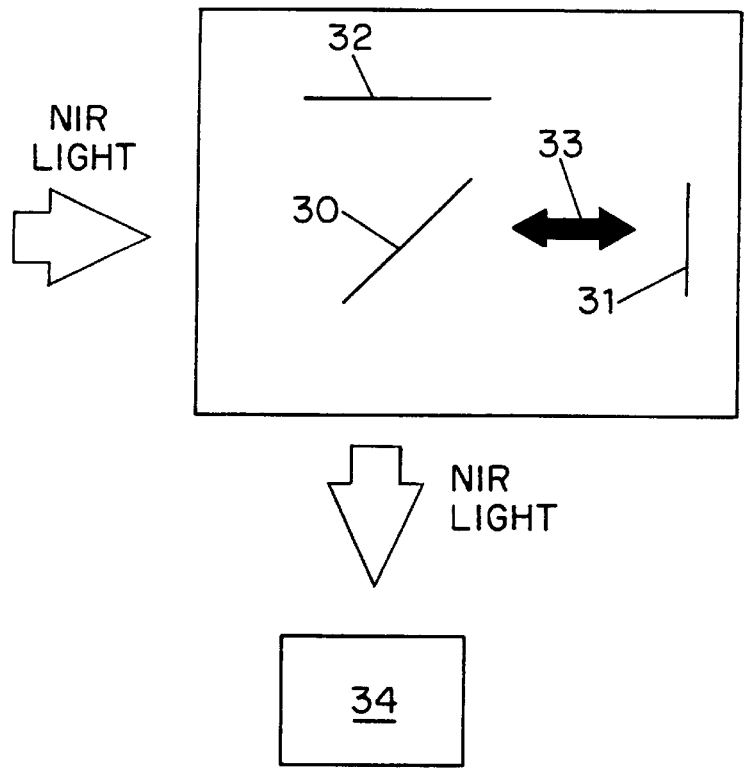
FIG. 3 is a schematic representation of an interferometer.
Figure 4:
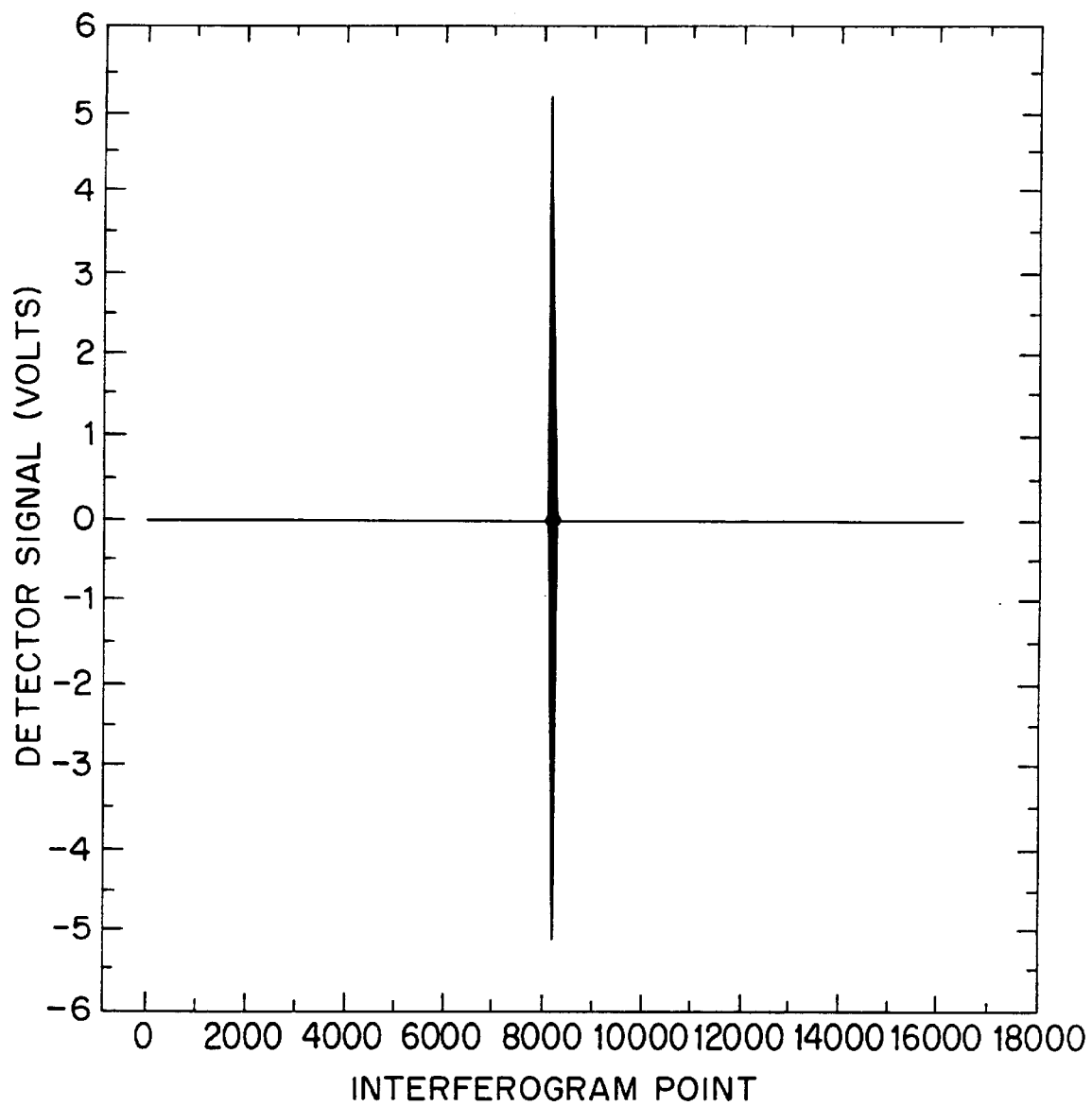
FIG. 4 shows a sample interferogram.

An interferometer such as that shown in FIG. 3 includes a 50:50 beam splitter 30, two mirrors 31 and 32, and optical track 33 and a detector 34. Infrared radiation is passed through the beam splitter 30 and directed toward the two mirrors 31 and 32, oriented at 90 degrees to one another, which reflect it back towards the detector 34. At the same time, the mirror 31 is moved back and forth on the optical track 33. The movement of the mirror 31 results in successive occurrences of constructive and destructive interference. Thus, the signal received at the detector is a harmonic signal whose frequency is determined by the frequency of incident light and the mirror velocity. A sample of the detected signal, called an interferogram, is shown in FIG. 4.

Interferograms can be converted by a mathematical transform into conventional spectra of very high quality. However, the mechanical complexity of the interferometer, and particularly the need for precise control of the movement of the mirror over a substantial length of travel and for precise optical alignment, limits the applicability of interferometers in rigorous environments. The mechanical complexity of the instrument could be substantially reduced if the length of the interferogram were shortened, because the length of mirror travel could be shorter. It is generally recognized, however, that the use of short interferograms significantly reduces the quality of the spectrum which can be obtained upon transformation of the interferogram to a conventional absorbance spectrum.

The reason for this loss of quality has to do with the mathematical approximation normally used to perform the transformation, the fast Fourier transform or FFT. The FFT is an approximation of the infinite Fourier integral in which it is assumed that the time signal is zero outside the region actually sampled. Supplying a very short interferogram to the FFT has the effect of convolving a boxcar function with the true (i.e. infinitely sampled) interferogram. The Fourier transform of the boxcar function is a (sin x)/x function. When this function is superimposed on the true spectrum, a lowering of resolution results.

In conventional interferometers in use today, the total travel of the mirror is around 2 cm, with spectral collection actually occurring over approximately 1 cm of this length. It has surprisingly been found, however, that short interferogram segments, i.e., interferograms collected over distance of mirror travel of about 0.003 to 0.10 cm can be used effectively in the method of the present invention. This opens the door to the construction of interferometers that are smaller and inherently more rugged than their laboratory predecessors, and which thus are suited for use, e.g., by an individual diabetic in the home.

A further advantage of the method as of the present invention is ability to dispense with separate background spectral measurements through the use of interferograms. Such measurements are necessary in most systems to correct for instrumental variations and the absorbance of compounds other than the compound of interest. In the case of non-invasive monitoring of physiological chemicals, however, this background is highly complex. Furthermore, it is not readily apparent how one would obtain a spectrum of the test subject, minus the chemical being analyzed. When using interferograms, however, no background is necessary. This is the case, because in an interferogram, the portion of the signal which can be attributed to the overall instrument function is a wide feature which is represented in the interferogram as a rapidly damping sinusoidal signal. In contrast, absorption bands of compounds are narrower and thus their interferogram representation does not damp as rapidly. Thus, by taking the analyzed data from an interferogram segment removed from the centerburst, the instrumentation dependent signal has essentially died out, leaving only the signals associated with actual infrared absorbances.

Regardless of the form of the collected data, the final step in the method as shown in FIG. 1 is the determination of glucose or other physiological chemical concentration by application of a previously determined mathematical (calibration) model. In either case, the input into the model is the filtered data, and the output is the estimated concentration of glucose or other physiological chemical of interest. The model is developed based upon a multivariate regression analysis, such as partial least squares (PLS) regression. In PLS, the independent variables are the filtered data and the dependent variable is the glucose concentration. Other multivariate regression methods such as principal components regression can also be used.

The mathematical model resulting from application of any of these techniques to a set of data in which the actual glucose concentrations are known can be expressed as a series of terms the value of which correspond to measured properties of the data for a sample, and factors or regression coefficients. For example, a model found to be useful in determining glucose concentrations in vivo using data in absorbance spectrum form has the form $$c_i = b_0 + b_1 x_{i,1} + \ldots + b_h x_{i,h}$$

where $c_i$ is the predicted glucose concentration corresponding to spectrum i, the $x_i$ values are the partial least-squares factor scores computed from the absorbance data, and the b terms are the coefficients determined from a multiple linear regression analysis of the measured glucose concentrations corresponding to the calibration absorbance data and the h sets of partial least-squares scores computed from the calibration absorbance data.

To analyze an unknown sample, values measured for the sample are substituted into this equation to produce an estimate of the glucose concentration in the sample. As a general rule, device limitations will probably require that this model be established for each chemical being measured using instrumentation separate from the device actually being used by a test subject to perform day-to-day monitoring. Nevertheless, some calibration function may be included in an individual device to adapt it to a specific test subject.

While the method of the invention has been described principally with respect to the monitoring of glucose in a human subject, the scope of the invention is not so limited. Physiological chemicals other than glucose, such as urea, lactate, triglycerides, total protein and cholesterol may also be quantitatively detected using the method of the invention through the selection of appropriate digital filtering parameters. Furthermore, because the filtering is all post-collection processing performed on stored data, a single spectrum can be analyzed numerous times to provide analytical results on more than one physiological chemical.

Test subjects to which the method of the invention may be applied include not only human subjects, but also animal subjects, e.g., during veterinary procedures, and even living plants. For example, non-invasive determination of sugar levels within fruits could be made to assess the ripeness of the fruit and its readiness for harvesting. Thus, as used in the specification and claims hereof, the term test subject refers to any living organism containing physiological chemicals.

Figure 5:
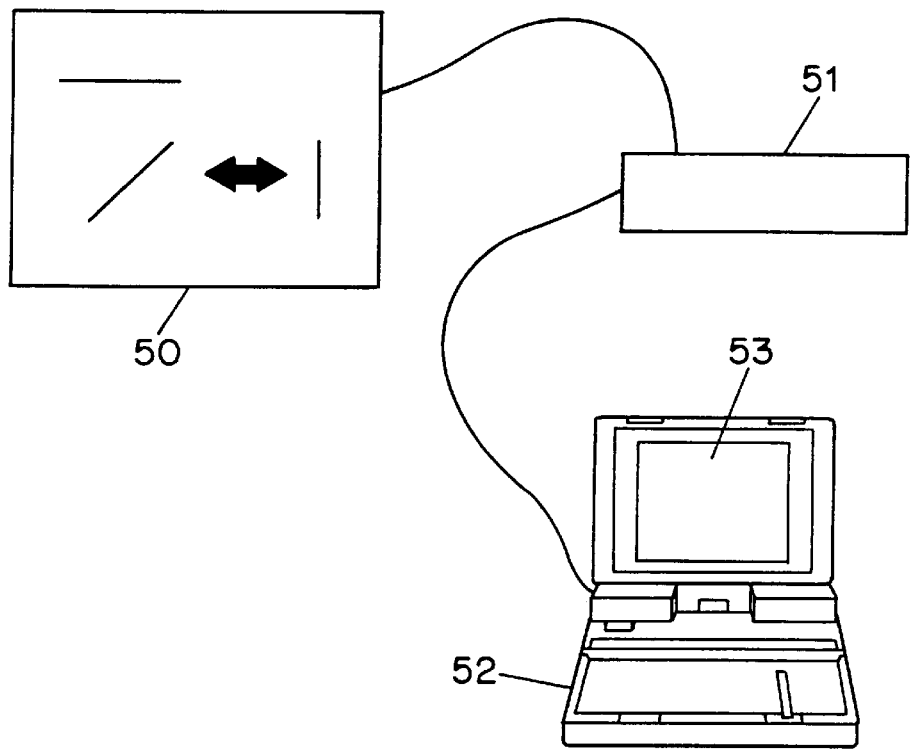
FIG. 5 shows a device in accordance with the present invention for measurement of glucose in a sample.

A further aspect of the present invention is a device for measurement of glucose in a sample as shown in FIG. 5. This device, which can be used on any type of sample, not just a living organism, includes means for collecting a transmitted or reflected infrared radiation such as interferometer 50 or a combination of a dispersive element and an optical multichannel analyzer. The collected spectral data is transferred to a computer readable storage medium 51 from whence it is read by computer processor 52 and processed in accordance with a programmed instruction to digitally filter the collected spectrum to isolate a portion of the spectrum indicative of glucose. Suitable computer processors for use in this application include Intel 486 and Pentium® microprocessors or MIPS R3000 and R4000 processors of the type used in Silicon Graphics workstations.

The computer program used to perform the digital filtering steps can be written in any programming language capable of performing a Fourier transform and multiplying a data set by a Gaussian function. For example, a program written in Fortran 77 was employed to perform the data analysis described in the example herein.

Once the stored data have been digitally filtered, the computer processor 52 is operated under a second set of programmed instructions in order to apply a predetermined mathematical model to the data. The result of this application is a numeric estimate for the concentration of glucose or other chemical of interest in the test subject.

The device of the invention also includes one or more means for reporting the amount of glucose in the sample. Examples of means for reporting the amount of glucose include digital display panels 53, transportable read/write magnetic media such as computer disks and tapes which can be transported to and read on another machine, and printers such as thermal, laser or ink-jet printers for the production of a printed report.

A further aspect of the present invention is an apparatus for the non-invasive, quantitative detection of physiological chemicals in living organisms. Such an apparatus may be a combination of a device for glucose measurement as described above, or a comparable device having the digital filter parameters and standard values targeted for a different physiological chemical with a means for irradiating the surface of the living organism with near-infrared radiation in such a way that the spectral data can be collected in a transmittance, diffuse reflectance or transflectance configuration.

Figure 6A:
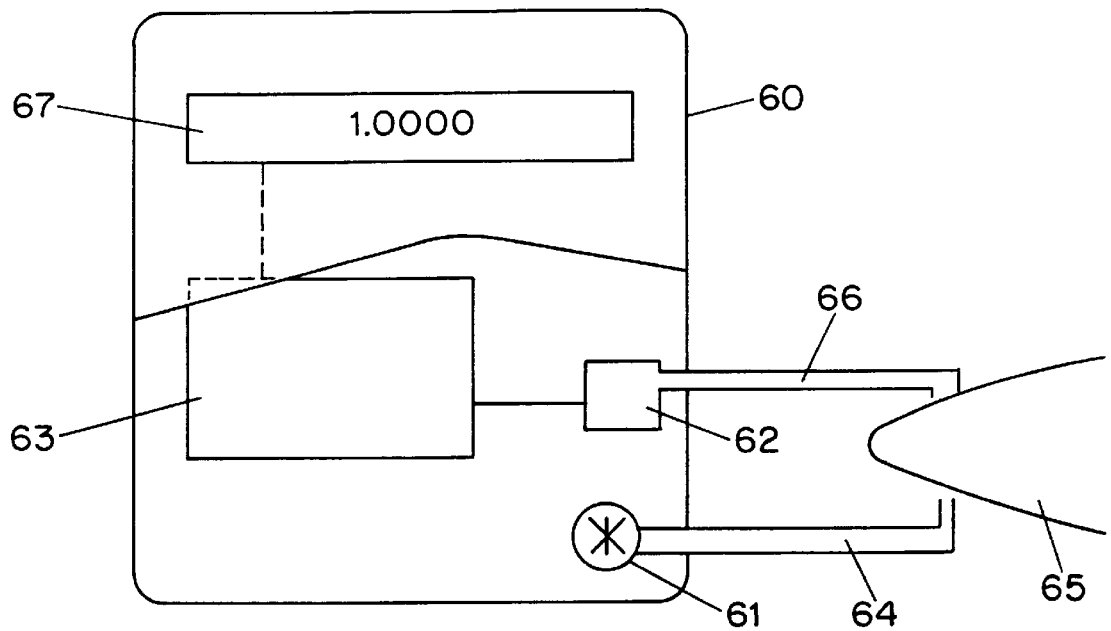
FIG. 6a and 6b show an apparatus in accordance with the present invention for non-invasive monitoring of physiological chemicals in a test subject.

FIG. 6A shows an apparatus of this type for collecting spectral information. The apparatus has a housing which encloses a light source 61, a detector 62, and a microprocessor 63. Infrared radiation from light source 61 is transmitted through optical fiber 64 to the test subject 65. Transmitted radiation is collected through optical fiber 66 and transmitted to detector 62. The signal from the detector is then transmitted to microprocessor 63. Microprocessor 63 digitally filters the signal from the detector, and applies the predefined mathematical model to the filtered data to determine a value for glucose concentration which is displayed on display 67. Display 67 may be an LED or LCD display.

Other configurations of the apparatus can be utilized in addition to the specific configuration shown in FIG. 6A. For example, the apparatus can be configured to collect infrared radiation in a diffuse reflectance mode, rather than in a transmission mode. In the diffuse reflectance mode, a portion of the incident radiation penetrates a short distance into the sample before being scattered out of the sample. A fraction of this back-scattered radiation is collected and measured by the detector.

Figure 6B:
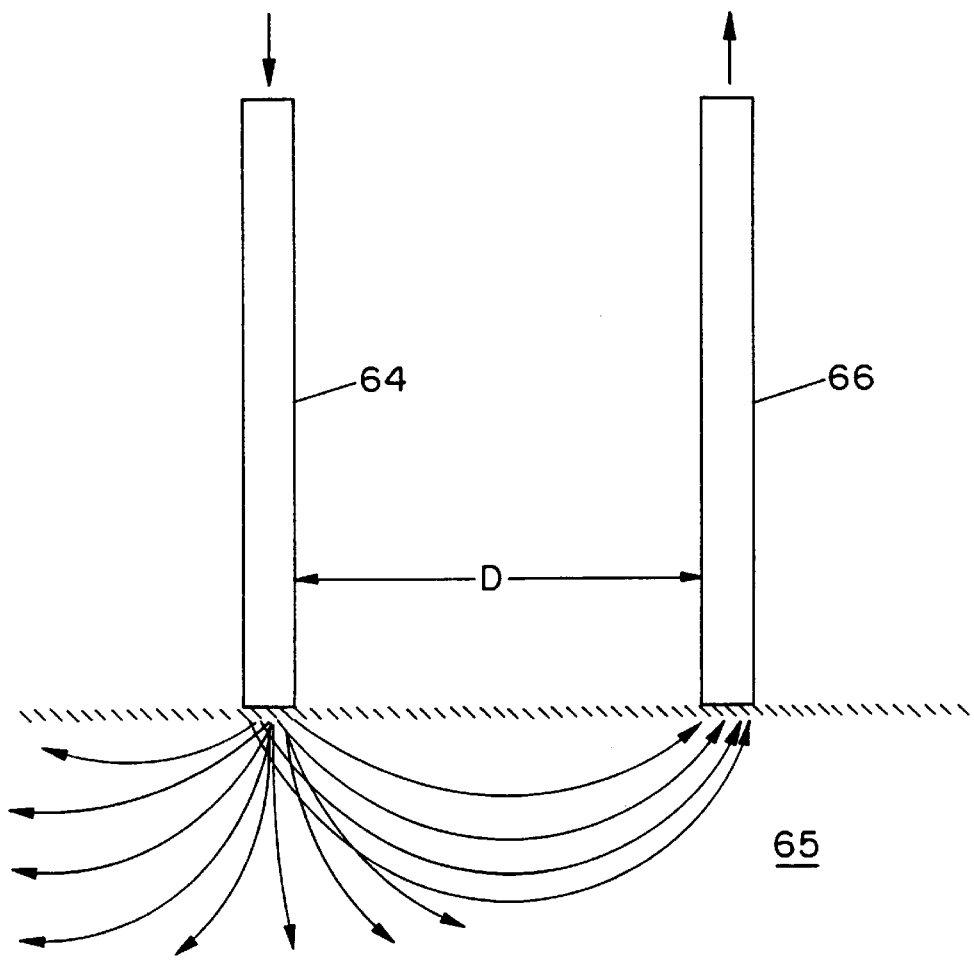

The apparatus may also be operated in a transflectance mode. In a transflectance configuration, optical fibers 64 and 66 are positioned apart by a distance D as shown in FIG. 6B. The second fiber collects light that has entered the sample and traversed a short distance within the sample medium.

EXAMPLE 1

In vitro measurements of glucose concentration were made on a series of thirteen glucose samples having concentrations varying from 1.25 to 19.7 mM glucose in pH 7.4 phosphate buffer (0.1 M). The samples were placed in 1 mm pathlength cuvettes constructed from infrared quartz and transmittance interferograms of each were obtained using a Nicolet 740 spectrometer in conjunction with a tungsten-halogen light source and a cryogenically cooled InSb near-infrared detector. Double sided interferograms were collected by averaging across 256 co-added scans. Either two or three replicate interferograms were made for each sample, producing a total of 38 interferograms across the 13 samples.

To evaluate glucose concentration, the glucose absorption located at 4400 cm$^{-1}$ was used and isolated by digital filtering. The filtering process involved application of a fast Fourier transform to the interferogram to produce a single beam spectrum; multiplication of the transformed interferogram with a Gaussian function having half-power points at 4445.6 and 4354.6 cm$^{-1}$; and application of the inverse fast Fourier transform to obtain the filtered interferogram.

Figure 7:
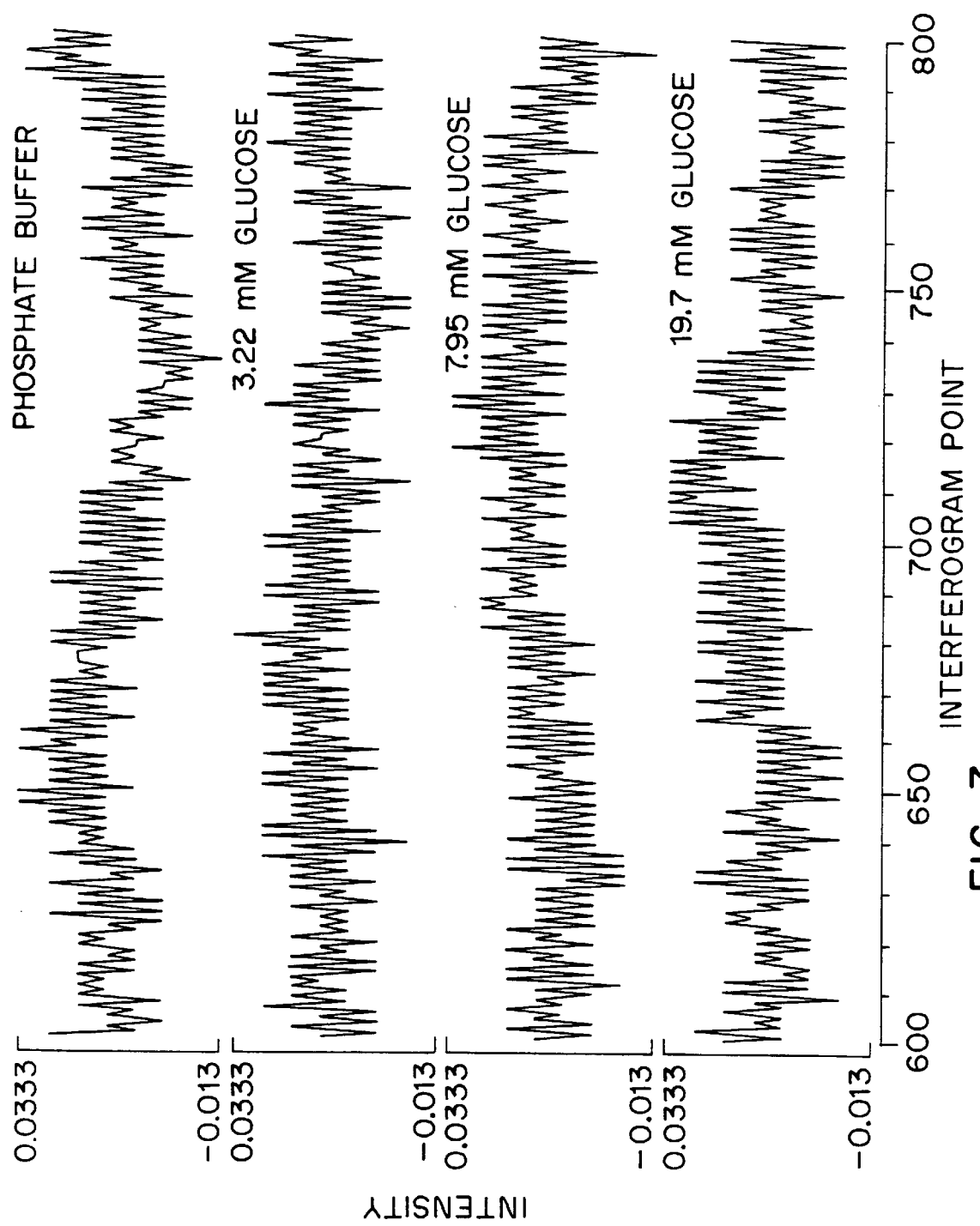
FIG. 7 shows unfiltered interferogram segments taken of phosphate buffer and three concentrations of glucose.
Figure 8:
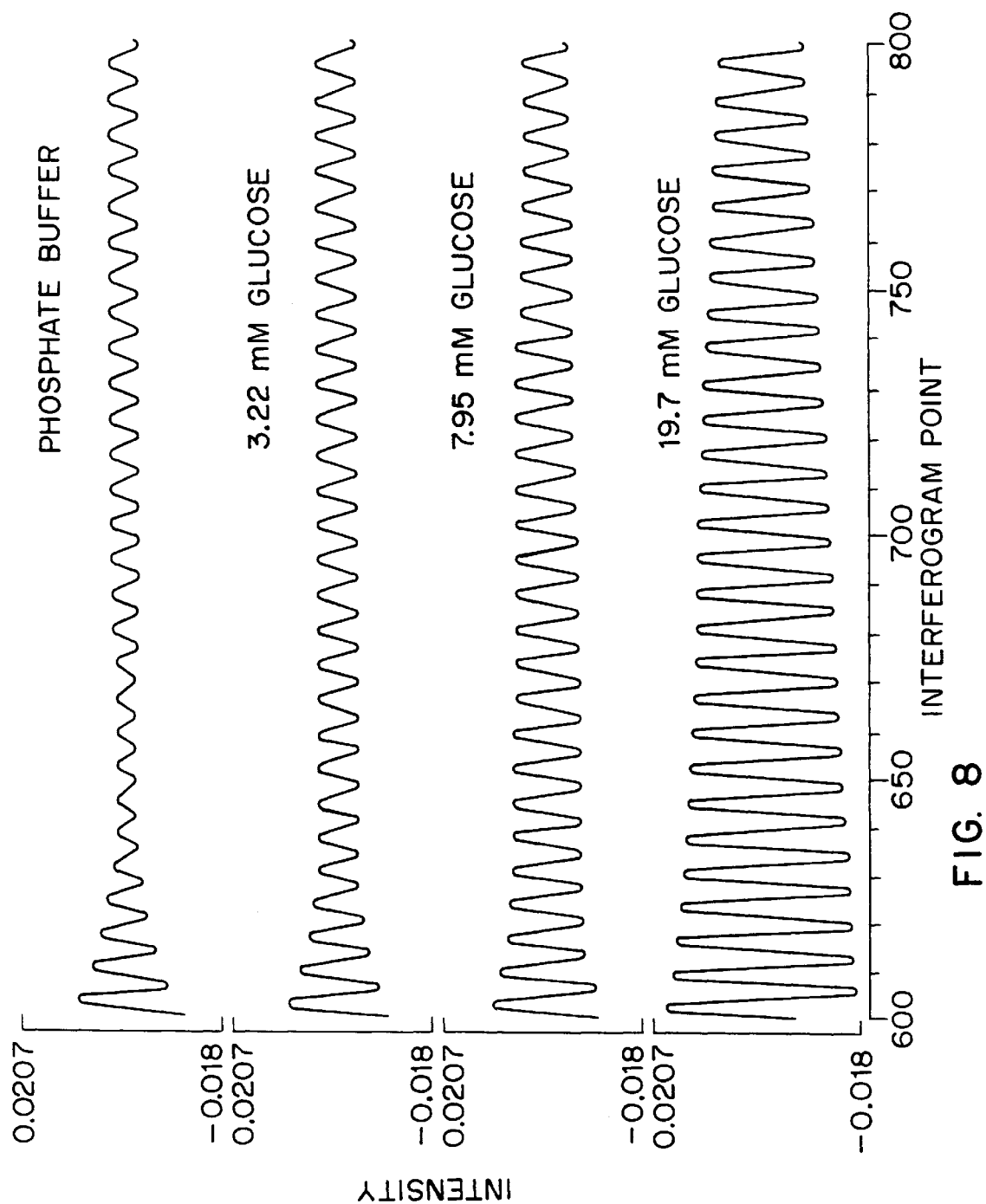
FIG. 8 shows digitally filtered interferogram segments taken of phosphate buffer and three concentrations of glucose.

FIG. 7 shows four interferograms segments (points 600–800 relative to the interferogram peak maximum or centerburst) obtained for phosphate buffer, 3.22 mM glucose, 7.95 mM glucose and 19.7 mM glucose. No obvious information relating to glucose concentration can be observed. FIG. 8 shows these same interferograms after the digital filtering procedure described above. The waveforms have been greatly simplified due to the removal of all frequencies outside the bandpass of the Gaussian function. The interferogram segment for the buffer decreases in intensity to a minimum point or node, followed by a slowly damping signal due to the water absorption feature. The interferograms of samples containing glucose exhibit a less obvious node, but increased magnitudes are observed with increasing glucose concentrations.

Figure 9:
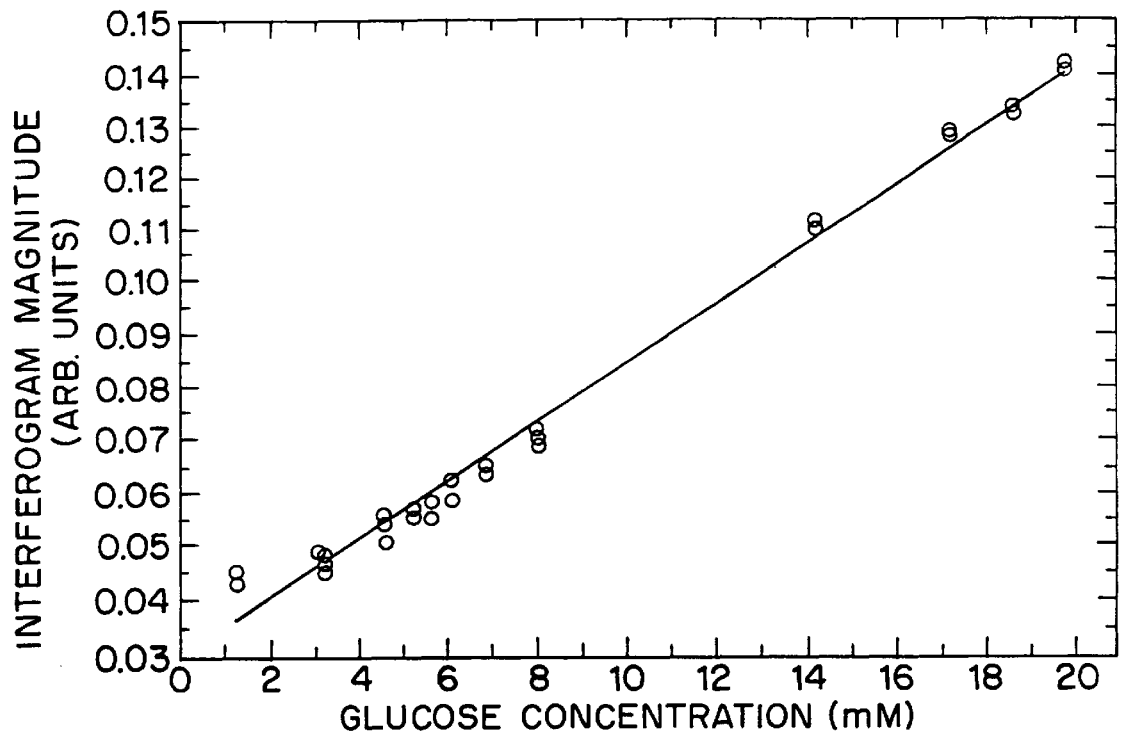
FIG. 9 shows the relationship between filtered interferogram segment magnitude and actual glucose concentration.

FIG. 9 shows the results obtained when the magnitudes of the filtered interferograms are plotted as a function of actual glucose concentration. An excellent correlation between the magnitude and the concentration is observed (Univariate linear regression: R squared=99.0%; standard error of calibration=0.62 mM).

EXAMPLE 2

In vivo experiments on the non-invasive detection of glucose were performed using a Nicolet 740 research grade spectrometer configured with a 250 W tungsten halogen lamp, $CaF_2$ beam splitter and InSb detector. Non-invasive measurements in accordance with the invention were taken at the same time as conventional invasive measurements on three individuals of varied physiognomy during the course of glucose tolerance tests. The beam of light from the spectrometer having a spectral range from 7000 to 5000 $cm^{-1}$ was passed through a portion of the webbing between the thumb and forefinger This particular wavenumber region was isolated using a standard astronomical H-band optical filter.

The spectra were collected in interferogram form using the interferometer and InSb detector of the spectrometer, and then converted to single beam spectrum (intensity versus wavenumber) using the accompanying Nicolet computer. All single beam spectra were subsequently transferred to a Silicon Graphics Indigo computer for data processing.

Blood samples taken during the test were analyzed for glucose using a Yellow Springs Instruments (YSI) model 2300 glucose analyzer.

To process the spectra, the single beam spectra were first converted to absorbance units by dividing each spectrum by a water reference spectrum and then computing the negative logarithm. Only the portion of the spectrum between 6500 and 5800 $cm^{-1}$ was used in all subsequent calculations.

Spectra were then normalized using the signal between 5955 and 5951 $cm^{-1}$, a wavenumber region that contains no glucose information. The normalized spectra were then digitally Fourier filtered to eliminate noise and other spectral features that distract from glucose information.

The first step in the Fourier filtering process was to perform a Fourier transform on the absorbance spectrum. This resulted in a Fourier domain spectrum, which was then multiplied by a Gaussian function defined by a mean position of 0.037 f and a standard deviation width of 0.011 f. These parameters were selected to isolate the glucose absorption. The filtered transformed spectrum was then converted back to an absorbance spectrum by applying an inverse Fourier transform.

The spectra obtained in this way were analyzed using the standard PLS regression procedure. This procedure essentially goes into the data set and weights the different spectral frequencies by correlating spectral variation with analyte concentration. The result is a series of factors and regression coefficients which can be applied to individual spectra to obtain a predicted value of glucose concentration.

Figure 10:
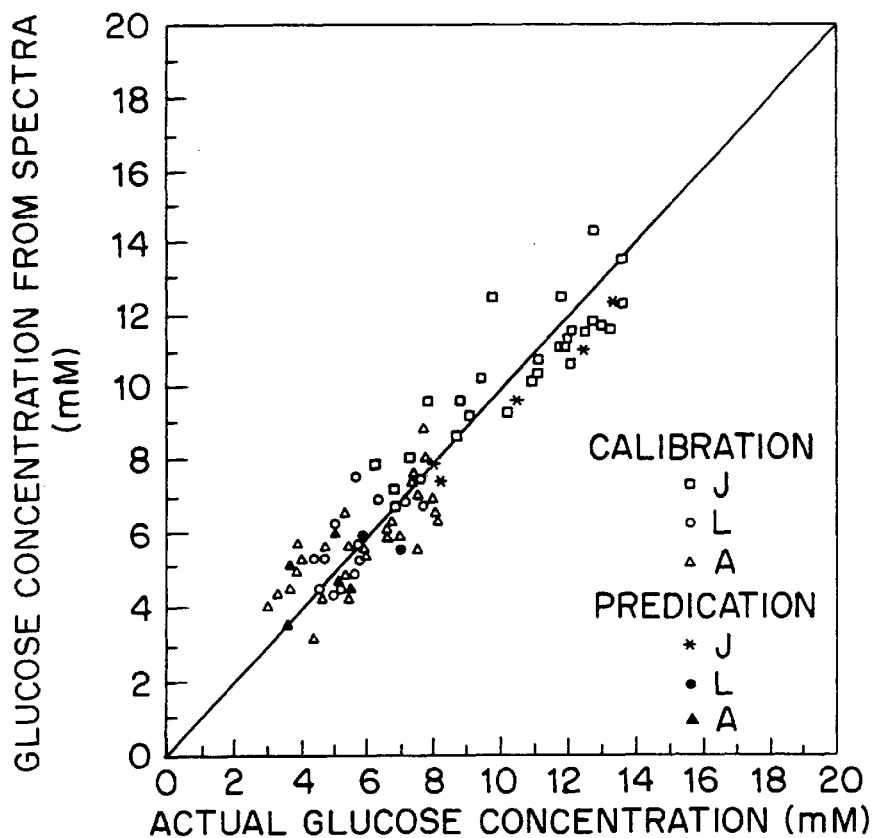
FIG. 10 shows the relationship between glucose concentration determined from digitally filtered absorbance spectra of human test subjects and actual glucose levels as determined by blood testing.

FIG. 10 shows the correlation between glucose concentration as determined from the spectra and the glucose level as determined from the blood samples taken. The open symbols in the graph represent the data that were used to generate the calibration model. The solid symbols represent results from an independent set of spectra used only for prediction purposes.

All of the results cluster around the unity line, and the prediction points are within the general spread and scatter of the calibration points. Thus, the ability of the method of the invention to predict blood glucose levels is confirmed. Moreover, since there is no clustering of data according to individual, a global calibration rather than individual calibrations may be possible.

EXAMPLE 3

Figure 11:
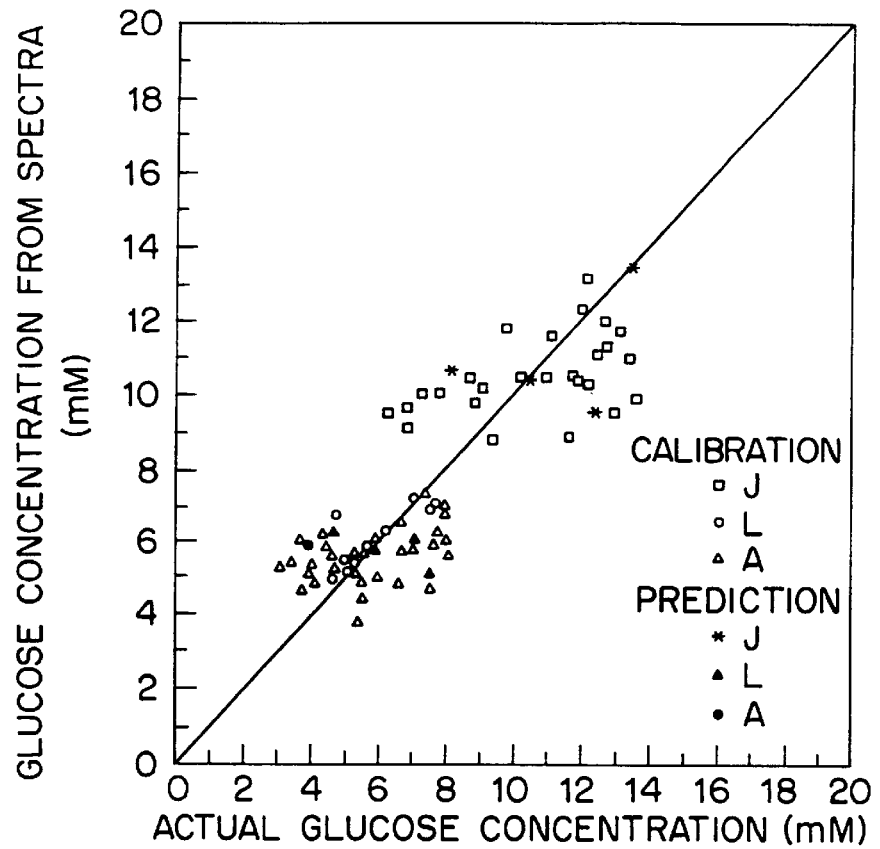
FIG. 11 shows the relationship between glucose concentration determined from unfiltered absorbance spectra of human test subjects and actual glucose levels as determined by blood testing.

To evaluate the importance of the digital filtering step in Example 2, the data taken in that experiment were reevaluated with the digital filtering step omitted and a separate set of PLS factors were developed. The resulting plot of spectral glucose versus blood glucose measurements is shown in FIG. 11. As is apparent, the data in this case has a much poorer correlation. Thus, the importance of an appropriate digital filtering technique is clear.

EXAMPLE 4

To test the validity of the derived linear relationship between concentration and interferogram peak magnitude, a series of preliminary experiments were performed using solution samples of benzene in $CS_2$. $CS_2$ has essentially zero absorbance in the region of the C–H out-of-plane bending band of benzene at 1036 $cm^{-1}$ that was used as the targeted band for the analysis. The linear approximation described above and a simple univariate model were successful in relating the magnitude of the filtered interferogram segments to concentration.

A second series of tests were run using samples of glucose in phosphate buffer. The glucose C–H combination band centered at 4400 $cm^{-1}$ was used as the targeted band for the analysis. This band is located on top of a broad background absorbance of water spanning the 4000–5000 $cm^{-1}$ region, and thus presents a greater challenge since it violates the assumption made in deriving the linear relationship that only a single absorbing species would be detected within the filter bandpass.

Calibration results made using the univariate linear approximation exhibited substantial errors. Since the information in the interferograms representing glucose and water should still be additive, however, it was hypothesized that a multivariate calibration model could be used to correct for the interference due to water. Partial least squares regression was used to build models of the form $$C=b_0+b_1x_1+ \ldots +b_nx_n$$

where C is glucose concentration and the n+1 $b_i$ values are regression coefficients determined from a multiple linear regression analysis of the calibration data set. The independent variables, $x_i$, are factor scores obtained from the PLS analysis of the filtered interferogram segment. The original independent variables used to obtain these latent variables are the intensities of the individual points in the filtered interferogram segment.

This approach was highly successful, yielding excellent glucose calibration models. Models based on three PLS factors were typically found to be optimal. Standard errors of calibration and prediction for these models after optimization of the bandpass filter wavelength and width and the region of the interferogram being analyzed ranged from 0.4 to 0.5 mM.

EXAMPLE 5

Direct analysis was performed on interferogram data for mixtures of glucose, bovine serum albumin (BSA) and triacetin in pH 7.4, 0.1 M phosphate buffer. This synthetic matrix provides many of the challenges of an actual biological matrix, while offering control and reproducibility. In particular, this matrix is challenging because both BSA and triacetin have significant absorption in the 4000–5000 $cm^{-1}$ range.

As in the analysis of glucose in phosphate buffer described in Example 4, multivariate calibration models were necessary to account for the presence of multiple absorbing species. In addition, utilization of multiple filters centered on different parts of the spectral region of interest was found to be effective.

Figure 12:
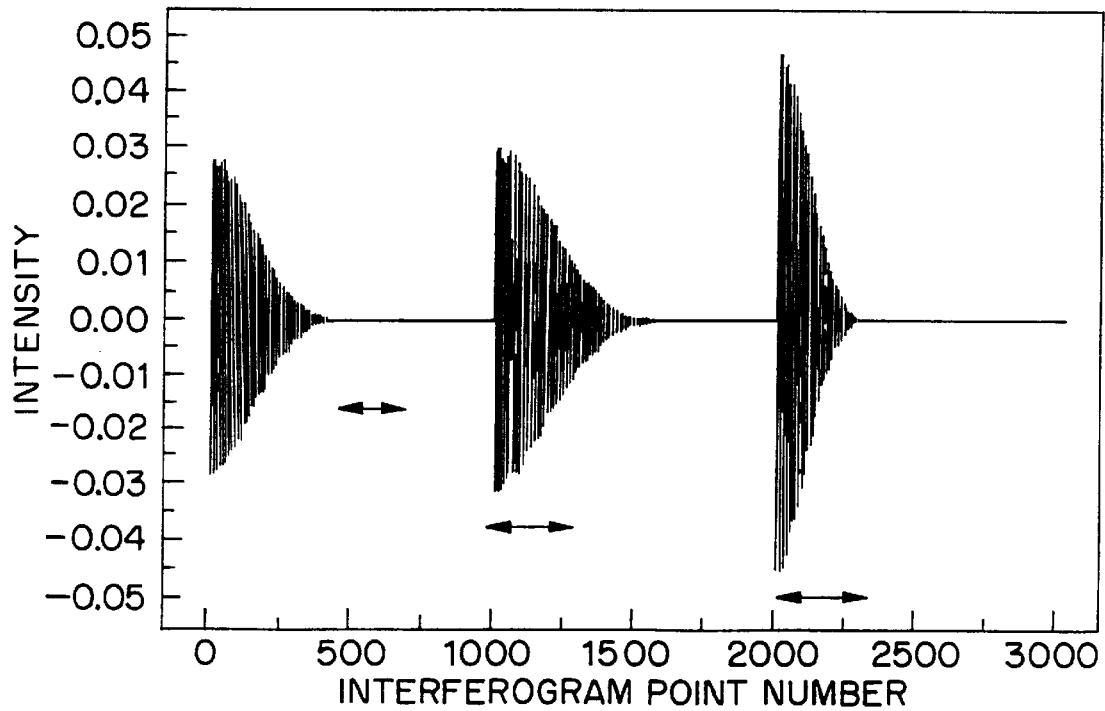
FIG. 12 displays the data obtained from applying three distinct filters to an interferogram obtained from a glucose/BSA/triacetin sample.

Specifically, filters of various widths which were centered on the glucose band at 4400 cm$^{-1}$, the BSA band at 4600 cm$^{-1}$, and the triacetin band at 4440 cm$^{-1}$ were studied. Each filter was applied to the raw interferogram, producing one, two or three filtered interferograms depending on the number of filters used. Segments of these filtered interferograms were then used together in PLS analysis FIG. 12 displays the data obtained from applying three distinct filters to an interferogram obtained from a glucose/BSA/triacetin sample. Segments of 1000 points from each of the three filtered interferograms are plotted, with the segments obtained by use of the glucose, BSA and triacetin filters being plotted as points 1–1000, 1001–2000 and 2001–3000, respectively. Shorter segments of each of these regions (denoted by the arrows in FIG. 12) were then investigated.

For cases using two and three filters, optimization of eight and twelve experimental variables is required, respectively. For each filter, the optimal bandpass position and width must be found, as well as the optimal interferogram segment location and length. This process involves repetitive calculations on standard data sets and evaluation of which factors provide the best ultimate calibration set.

Figure 13:
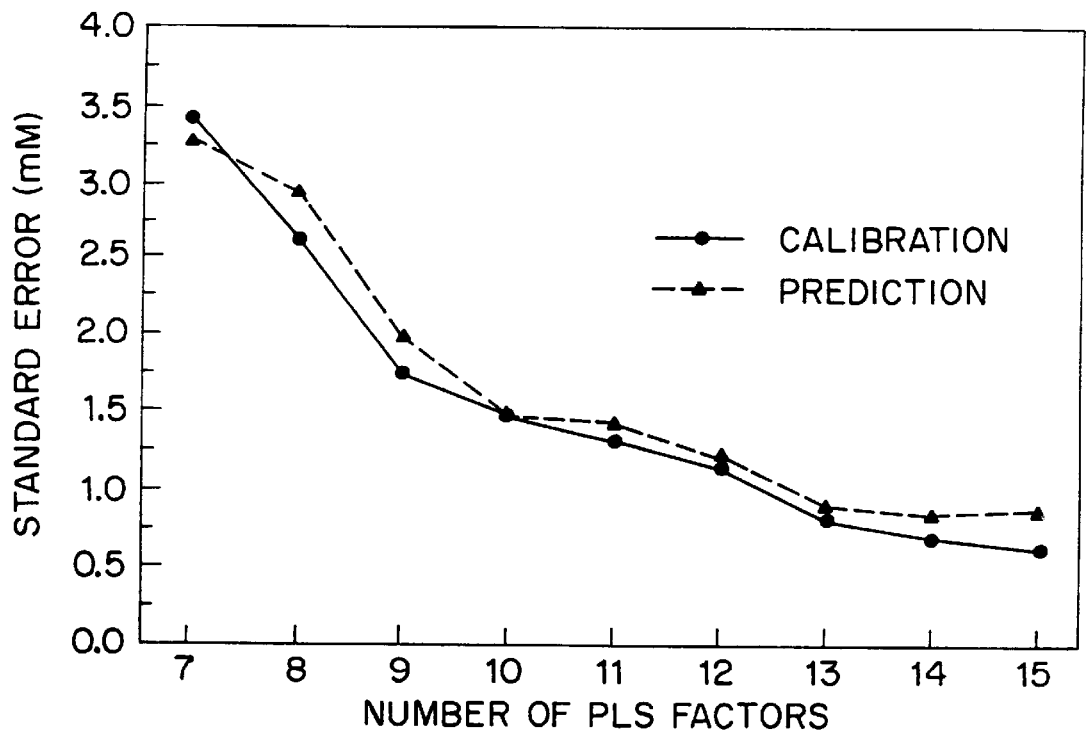
FIG. 13 plots the standard error of calibration (solid line) and prediction (dashed line) versus the number of PLS factors used to form the calibration model of a filtered interferogram in a two-filter analysis based on interferogram points 340–640 for the glucose filter and points 200–301 for the BSA filter.

FIG. 13 plots the standard error of calibration (solid line) and prediction (dashed line) versus the number of PLS factors used to form the calibration model in a two-filter analysis based on interferogram points 340–640 for the glucose filter and points 200–301 for the BSA filter. The optimal model size in this case is 14 terms. This model exhibited an R$^2$ value of 98.45%, and standard errors of calibration and prediction of 0.704 and 0.841 mM, respectively.

Figure 14:
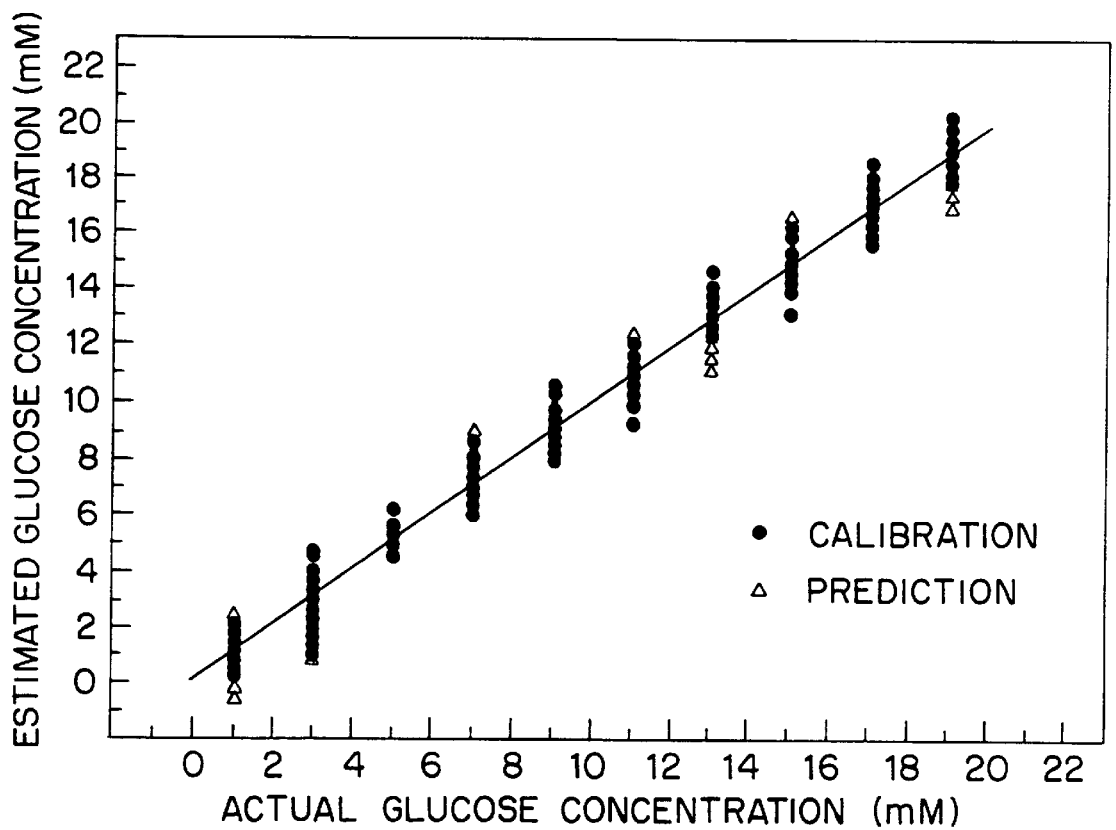
FIG. 14 is a correlation plot of glucose concentrations estimated using a 14 term calibration model versus the corresponding actual concentrations.

FIG. 14 is a correlation plot of glucose concentrations estimated using this 14 term calibration model versus the corresponding actual concentrations. Calibration samples are indicated by closed circles, while prediction samples are indicated by open triangles. Inspection of this data reveals that the prediction data falls within the span of variation of the calibration data and that a strong correlation exists between estimated and actual concentrations.

Examination of residuals from the model reveals no relationship between residuals and either BSA or triacetin concentration. There is some evidence of nonlinearity in the plot of residuals versus estimated concentrations, however. This suggests that the presence of signals from multiple absorbing species within the filter bandpass has violated the assumptions of the linear approximation equation set forth above.

EXAMPLE 6

Figure 15:
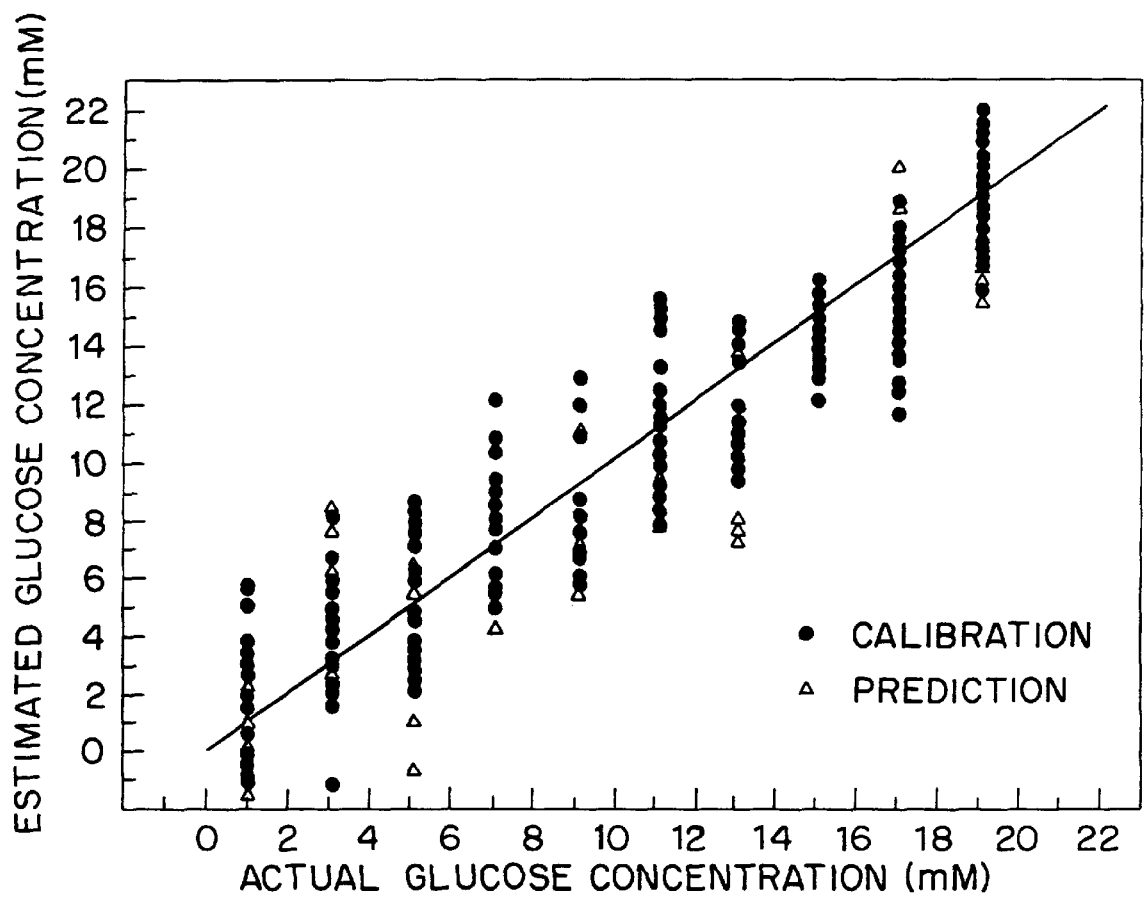
FIG. 15 is a correlation plot of glucose concentrations estimated using a 15 term calibration model for an unfiltered interferogram versus the corresponding actual concentrations.

The use of multivariate calibration models provides the ability for the model itself to extract signals from overlapping information in the interferogram. This raises the question as to whether the digital filtering step is necessary. To address this question, an optimization was conducted to identify the best segment in the unfiltered spectrum for use in building a multivariate calibration model. The best model found was based on interferogram points 100–450 and included 15 PLS factors. FIG. 15 is a correlation plot analogous to FIG. 14 for this model. As can be seen, the standard errors of calibration and prediction have both increased by a factor of approximately three, and significantly greater scatter exists in the data points. Thus, it appears that the filtering step is essential to obtaining good calibration models from the interferogram data.

We claim:

1. A method for non-invasive quantitative detection of a physiological chemical in a test subject comprising the steps of:
   (a) irradiating an exterior surface of a portion of the test subject with near-infrared radiation such that the radiation is transmitted through or reflected from the portion of the test subject;
   (b) collecting data concerning the infrared radiation transmitted through or reflected from the portion of this subject using a detector, wherein the collected data is from an absorbance spectrum or an interferogram;
   (c) digitally filtering the collected data to isolate a portion of the data indicative of the physiological chemical; and
   (d) determining the amount of physiological chemical in the test subject by applying a defined mathematical mode to the digitally filtered data.

2. A method according to claim 1, wherein the digital filtering is performed by a Fourier filtering process.

3. A method according to claim 1, wherein the collected data is in the form of an absorbance spectrum.

4. A method according to claim 3, wherein the spectrum is digitally filtered by performing a Fourier transform on the absorbance spectrum; multiplying the transformed spectrum by a Gaussian function; and applying an inverse Fourier transformation to the multiplied transformed spectrum.

5. A method according to claim 4, wherein the mathematical model applied to the digitally filtered spectrum applies coefficients developed using a partial least squares regression multivariate calibration procedure.

6. A method according to claim 5, wherein the spectrum that is digitally filtered spans the region from 6500 to 5800 cm$^{-1}$.

7. A method according to claim 6, wherein the magnitude of the digitally filtered spectrum is compared to a standard value using a series of regression coefficients developed using a partial least squares regression multivariate calibration procedure.

8. A method according to claim 1, wherein the collected data is in the form of a single beam spectrum.

9. A method according to claim 1, wherein the collected data is in the form of an interferogram.

10. A method according to claim 9, wherein only a short segment of an entire interferogram is analyzed.

11. A method according to claim 10, wherein the digital filtering step comprises the steps of performing a fast Fourier transform on the interferogram to obtain a transformed spectrum; multiplying the transformed spectrum with a Gaussian function to select for a peak diagnostic for the physiological chemical; and applying an inverse Fourier transform to the multiplied, transformed spectrum.

12. A method according to claim 11, wherein the Gaussian function is selected to isolate the glucose-associated absorbance at 4400 cm$^{-1}$.

13. A method according to claim 9, wherein the digital filtering step comprises the steps of performing a fast Fourier transform on the interferogram to obtain a transformed spectrum; multiplying the transformed spectrum with a Gaussian function to select for a peak diagnostic for the physiological chemical; and applying an inverse Fourier transform to the multiplied, transformed spectrum.

14. A method according to claim 1, wherein the collected data is an interferogram and the digital filtering is performed directly on the interferogram to select out waveforms within the interferogram having a frequency equal to $$\frac{frequency}{of\,signal} = 2 \times \frac{wavenumber}{of\,radiation} \times \frac{mirror}{velocity}$$

where the wavenumber has units of cm$^{-1}$, mirror velocity is the velocity of mirror travel in the interferometer used to generate the interferogram expressed in units of cm/sec.

15. A method according to any of claims 1–5 or 6–14, wherein the chemical is glucose.

16. An apparatus for the non-invasive measurement of one or more physiological chemical in a test subject, comprising, (a) means for irradiating an exterior surface of a portion of the test subject with near-infrared radiation such that near infrared radiation transmitted through or reflected from the exterior surface of the portion of the test subject is available for collection;

(b) means for collecting data concerning the transmitted or reflected near-infrared radiation;

(c) means for digitally filtering the collected data to isolate a portion of the data indicative of the physiological chemical;

(d) means for applying a defined mathematical model to the digitally filtered data, whereby the amount of chemical in the test subject is determined; and (e) means for reporting the amount of chemical in the test subject.

* * * * *